United States Patent [19]
Ardaillon et al.

[11] Patent Number: 5,098,718
[45] Date of Patent: Mar. 24, 1992

[54] ENZYMATICALLY DEGRADABLE COATING COMPOSITIONS FOR FEED ADDITIVES INTENDED FOR RUMINANTS

[75] Inventors: Pierre Ardaillon, Saint-Priest; Christine Franzoni, Lyons, both of France

[73] Assignee: Rhone-Poulenc Sante, Atony Cedex, France

[21] Appl. No.: 536,403

[22] Filed: Jun. 11, 1990

[30] Foreign Application Priority Data

Jun. 12, 1989 [FR] France .................... 89 07717

[51] Int. Cl.⁵ .................................... A23K 1/00
[52] U.S. Cl. .......................... 426/2; 426/73; 426/74; 426/96; 426/302; 426/310; 426/656; 426/807; 424/438; 424/495
[58] Field of Search ............... 426/2, 73, 74, 96, 98, 426/302, 310, 807, 656; 424/438, 489, 495

[56] References Cited

U.S. PATENT DOCUMENTS

| | | |
|---|---|---|
| 4,675,175 | 6/1987 | Autant et al. . |
| 4,832,967 | 5/1989 | Autant et al. . |
| 4,851,509 | 7/1989 | Jolles et al. . |
| 4,876,097 | 10/1989 | Autant et al. . |
| 4,877,621 | 10/1989 | Ardaillon et al. . |
| 4,983,403 | 1/1991 | Ardaillon et al. ............. 426/2 |

FOREIGN PATENT DOCUMENTS

0188953 7/1986 European Pat. Off. .

Primary Examiner—R. B. Penland
Attorney, Agent, or Firm—Finnegan, Henderson, Farabow, Garrett, and Dunner

[57] ABSTRACT

Enzymatically degradable compositions for the coating of feed additives intended for ruminants, including zein, at least one hydrophobic substance, optionally at least one non-water-soluble polymer and at least one inorganic filler. The compositions are used to coat feed additives such as medicinal products, vitamins and amino acids.

22 Claims, No Drawings

ENZYMATICALLY DEGRADABLE COATING COMPOSITIONS FOR FEED ADDITIVES INTENDED FOR RUMINANTS

The present invention relates to coating compositions for animal feed additives. More particularly, the present invention relates to enzymatically degradable coating compositions for feed additives intended for ruminants.

Biologically active substances which are orally administered to ruminants typically undergo degradation in the rumen. These active substances consequently cannot fully exercise their activity upon degradation in the rumen, leading to a decreased effectiveness for their intended purpose. If these active substances are allowed to progress through the rumen and further down the digestive tract into the abomasum or even further into the small intestine and/or into the large intestine, the effectiveness of the active substances is relatively increased since the active substances are better absorbed in the abomasum, small intestine and large intestine. These active substances are typically formulated as food additives, and can constitute medicinal products, vitamins, amino acids and the like.

Several types of coating compositions for protecting these biologically active substances against degradation in the rumen are known. Among these types of compositions, coating compositions having the property of being stable in the rumen, where the pH is in the region of 6, while permitting relatively rapid release of the active substance in the abomasum, where the pH is in the region of 2, have been used.

In general, these known coating compositions are formulated with a substance sensitive to pH variations and at least one hydrophobic substance. The pH-sensitive substance is selected, in particular, from synthetic basic copolymers, such as from copolymers of styrene and vinylpyridine. The hydrophobic substances may be selected, for example, from fatty acids or their derivatives, and hydrophobic polymers. These coating compositions form a continuous film around the biologically active substance. Such compositions are described, for example, in French Patents FR 78/23,966 (2,401,620), FR 78/23,968 (2,401,621) and FR 81/18,954 (2,514,261).

The selection of the pH-sensitive substance is determinative of the potential substance's respective behavior as a function of pH. Specifically, the potential substance should render a coating composition that is stable at a pH not below 5.5 for a long period (24 to 48 hours) and that is rapidly degraded (a few minutes to a few hours) at a pH not exceeding 3.5. As a result, coating compositions whose difference in behavior at about pH 6 and at about pH 2 is small cannot be usable for an adequate coating composition.

Thus, in U.S. Pat. No. 4,876,097, coating compositions are disclosed which consist of a substance sensitive to pH variations and a non-water-soluble film-forming binder whose hydrophilicity is controlled. The comparative examples given therein show that, in the absence of the non-water-soluble film-forming binder or in the absence of the substance sensitive to pH variations, compositions are obtained which are, on the face of it, unusable for the desired objective since they have comparable stabilities at about pH 6 and at about pH 2. Another coating composition which is pH sensitive is disclosed in U.S. Pat. No. 4,877,621. Both of these patents utilize synthetic copolymers manufactured by polymerization of styrene and vinylpyridine. Before using the copolymer, it must be purified to eliminate all the starting monomers, which are not safe for animal nutrition. That elimination can be very difficult to carry out.

Although these types of known materials have proven useful, it has not been apparent that any of these compositions could overcome the problems inherent in these compositions, these problems being demonstrated by a relatively weak ability to protect biologically active substances from degradation in the rumen so that the active substance can progress further down the digestive tract and into the small intestine. A coating composition is desired which exhibits stability under the pH conditions of the rumen, which is relatively stable and not substantially degraded under the pH conditions of the abomasum, but which is strongly degraded by enzymes in the small intestine.

In accordance with the invention, a novel coating composition can be provided which is stable in the rumen, which is not substantially degraded in the abomasum, and which is strongly degraded in the small intestine as a result of enzymes encountered between the abomasum and the ileum. The degradation may not stop at the end of the small intestine, since there are no substantial differences in enzyme composition between the small intestine and the large intestine. Degradation which begins in the abomasum can continue through the small intestine and into the large intestine. In essence, degradation can occur, in varying degrees, all along the line of travel from the abomasum through the large intestine. Biologically active substances coated with these compositions substantially retain their beneficial activity during progress through the digestive tract, until degradation of the coating by enzymes present in the abomasum and in the small intestine is performed. Upon sufficient degradation of the coating, the biologically active substance is released.

In accordance with one embodiment of the invention, a coating composition for feed additives is provided, the composition containing zein, a hydrophobic substance, an optional non-water-soluble polymer and an organic filler. This coating composition is stable in the rumen, is not substantially degraded in the abomasum and is substantially degraded primarily by enzymes in the small intestine.

The hydrophobic substance can be fatty acids, fatty esters, fatty alcohols, and mixtures thereof. Preferred fatty acids can be stearic acid and behenic acid. The hydrophobic substance preferably has a melting point above about 60° C.

The non-water-soluble polymer can be non-water-soluble ethers and esters of cellulose, ethylcellulose, cellulose acetate, cellulose propionate, cellulose acetate butyrate, polyvinyl esters, polyvinyl acetate, and mixtures thereof. Ethylcellulose is preferred.

The inorganic filler can be talc, silica, carbonates, complex polyphosphates based on $Na_2O$, $CaO$, $P_2O_5$ and $Al_2O_3$, and mixtures thereof.

Further, a plasticizer, such as triacetin, butylphthalate, sodium oleate, propylene glycol and mixtures thereof, can also be used in the coating composition.

One preferred composition in accordance with the invention contains by weight in the range of about 10 to about 90% of the zein, in the range of about 10 to about 90% of the hydrophobic substance, in the range of about 0 to 80% of the non-water-soluble polymer, and in the range of about 5 to about 300% of the inorganic filler calculated relative to the combined weight of the zein, the hydrophobic substance and the non-water-soluble polymer.

Another preferred composition in accordance with the invention contains by weight in the range of about 30 to about 80% of the zein, in the range of about 10 to about 70% of the hydrophobic substance, in the range of about 0 to about 70% of the non-water-soluble polymer, and in the range of about 5 to about 150% of the inorganic filler calculated relative to the combined weight of the zein, the hydrophobic substance and the non-water-soluble polymer.

In accordance with another embodiment of the invention, a feed additive intended for ruminants is provided, which contains one or more cores of a biologically active substance surrounded by a substantially continuous film of a coating composition comprising zein, a hydrophobic substance, an optional non-water-soluble polymer and an inorganic filler. The coating composition is stable in the rumen, is not substantially degraded in the abomasum and is substantially degraded primarily by enzymes in the small intestine. The feed additive can be medicinal products, vitamins and amino acids, such as methionine, lysine, and vitamin A.

The biologically active substance can be in the range of, by total weight, about 40 to about 95% of the feed additive.

In accordance with another feature of the invention, the feed additives can be in the form of granules. The coating composition can be in the range of about 5 to about 60% by total weight of the granules. The granules can have a size in the range of about 0.1 to 5 mm, and preferably in the range of about 0.6 to about 2 mm.

In accordance with another embodiment of the invention, a method of administering a biologically active substance to a ruminant is provided, by the step of orally administering to the ruminant a sufficient amount of granules sufficient to deliver an effective amount of the biologically active substance. The granules consist of one or more cores of the biologically active substance surrounded by a substantially continuous film of a coating composition containing zein, a hydrophobic substance, an optional non-water-soluble polymer and an inorganic filler. The biologically active substance can be medicinal products, vitamins and amino acids. The oral administration is preferably in the form of feed additives.

One objective of the present invention is to ameliorate the disadvantages of the known compositions by proposing a coating composition which undergoes substantial degradation by enzymes in the small intestine, but which is stable in the rumen and is not substantially degraded in the abomasum.

To this end, the compositions according to the invention are especially useful for coating biologically active substances which are sensitive to degradation in the rumen. These coating compositions, consisting of substances which are known to be used in the food industry, provide a considerable advantage over previously-known compounds. These coating compositions typically do not require purification after manufacture and prior to administration to the ruminant.

These coating compositions are especially useful for coating active substances which are sensitive to degradation in the rumen, and are especially useful for protecting various therapeutic or nutrient biologically active substances, such as medicinal products, and vitamins and/or amino acids, such as methionine, lysine and vitamin A, intended for oral administration to ruminants.

According to the present invention, a biologically active substance which is to be orally administered to a ruminant is coated with a composition which is stable in the rumen, thereby implying good resistance to the microbial flora and to the enzymes of the rumen environment. The coating composition is also relatively stable and is not substantially degraded in the abomasum in which the pH is acid, although degradation can begin in the abomasum. Further, the coating composition is strongly degraded in the small intestine primarily by the enzymes encountered between the abomasum and the ileum. The degradation may not stop at the end of the small intestine, since there are no substantial differences in enzyme composition between the small intestine and the large intestine. Degradation which begins in the abomasum can continue through the small intestine and into the large intestine. In essence, degradation can occur, in varying degrees, all along the line of travel from the abomasum through the large intestine.

The biologically active substance can be orally administrated either directly or as a food additive, with the latter method of oral administration being preferred.

The coating compositions according to the invention include zein combined with a hydrophobic substance and optionally with a non-water-soluble polymer, and with an inorganic filler. Zein is used as a film-forming binder which can be destroyed by enzymes. The coating composition is stable in the rumen, relatively stable and not substantially degraded in the abomasum and substantially degraded in the small intestine primarily by enzymes. Stated another way, the coating composition is stable in the rumen, is not substantially degraded in the abomasum and is substantially degraded in the small intestine primarily by enzymes. The coating compositions are preferably developed to exclude the synthetic copolymers found in several known compositions, particularly copolymers manufactured by the polymerization of styrene and vinylpyridine. The coating compositions are especially useful for coating feed additives for ruminants.

The hydrophobic substance can be any suitable substance, and is preferably selected, for example, from fatty acids (such as stearic acid and behenic acid), fatty esters, fatty alcohols, and mixtures thereof. Stearic acid is most preferably used. The hydrophobic substance preferably has a melting point above about 60° C.

The optional non-water-soluble polymer can be any suitable polymer, and is preferably selected from non-water-soluble ethers or esters of cellulose, such as ethylcellulose, cellulose acetate, cellulose propionate or cellulose acetate butyrate, polyvinyl esters, such as polyvinyl acetate, and mixtures thereof. Ethylcellulose is most preferably used.

The inorganic filler can be any suitable filler, and is selected, in particular, from fillers, pH-sensitive or otherwise, and in particular from talc, silica, carbonates, complex polyphosphates based on $Na_2O$, $CaO$, $P_2O_5$ and $Al_2O_3$, and mixtures thereof. The inorganic filler can also assist in the liberation of the active substance.

According to a first preferred composition, the coating composition includes two components: (a) in the range of about 10 to about 90% by weight of zein, in the range of about 10 to about 90% of a hydrophobic substance, and in the range of about 0 to about 80% of a non-water-soluble polymer and (b) in the range of about 5 to about 300% of an inorganic filler calculated relative to the total weight of component (a) (that is, the combined weight of the zein, the hydrophobic substance, and, if present, the non-water-soluble polymer).

According to a second preferred composition, the coating composition includes two components: (a) in the range of about 30 to about 80% by weight of zein, in the range of about 10 to about 70% of a hydrophobic substance, and in the range of about 0 to about 70% of a non-water-soluble polymer; and (b) in the range of about 5 to about 150% of an organic filler calculated relative to the total weight of component (a) (that is, the combined weight of the zein, the hydrophobic substance and, if present, the non-water-soluble polymer).

The coating compositions for feed additives containing the biologically active substances and intended for ruminants can optionally contain, in addition, one or more plasticizers. The plasticizer can be any suitable substance and is preferably selected from triacetin, butylphthalate, sodium oleate, propylene glycol, and mixtures thereof.

The biologically active substance is preferably in the range by total weight, about 40 to about 95% of the feed additive.

Given the disclosure herein of the coating compositions in accordance with the invention, it is within the ordinary skill of the art to produce any material disclosed herein by employing as paradigms the examples given in the remainder of the description. For example, a suitable coating composition may be obtained by dispersing or dissolving appropriate weights of the zein, the hydrophobic substance, the filler and, when present, the non-water-soluble polymer, in a suitable organic solvent or in a mixture of suitable organic solvents selected in accordance with the specific nature of the constituents. These solvents can be dichloromethane, ethanol, glycols, formamide, alcohols mixed with water, ketones mixed with water, dioxane mixed with water, alcohols mixed with aromatic hydrocarbons, alcohols mixed with chlorinated hydrocarbons, alcohols mixed with nitro paraffins, alcohols mixed with glycols, alcohols mixed with esters, alcohols mixed with ketones, and the like, and mixtures thereof. In general, the coating composition is obtained after evaporation of the solvent or solvents.

The coated substances are generally added to the ruminants' feed in an appropriate manner. The coated substances are preferably granules in the form of microcapsules consisting of one or more cores of the specific biologically active therapeutic or nutrient substances surrounded by a continuous film of the coating composition. The coating composition preferably represents 5 to 60% by weight of the total granule.

The granules may be manufactured by techniques known to those skilled in the art. Depending on the specific formulation of the coating composition, microencapsulating or granules-forming techniques of either extrusion or spraying of solutions in a fluidized or agitated bed, or techniques of encapsulation in a molten or semi-molten medium, or techniques of coating in a liquid medium, such as coacervation, may be used.

The size of the resulting granules will be dependent on the use to which they are put, and will be determined, more especially, in accordance with the animal for which they are intended. It is possible to coat active substances which take the form of granules ranging in size from about 0.1 to about 5 mm, and preferably from about 0.6 to about 2 mm.

Of special importance are granules which contain, as active substances, methionine, lysine, vitamins, such as vitamin A, and mixtures thereof. These biologically active substances are very important in the care and feeding of animals in general, particularly ruminants.

An appropriate amount of these granules is orally administered to the ruminant, such as by a sufficient amount of granules being added to feed so that an effective amount of the granules are ingested by the ruminant. The feed with which the feed additives is preferably of solid form, such as grain. The feed additives enter into and through the rumen, travel down the digestive tract entering into and through the abomasum and eventually enters into the small intestine and possibly into the large intestine. The coating compositions in accordance with the invention are relatively stable and are not substantially degraded in the abomasum, and are substantially degraded in the small intestine as a result of the enzymes encountered between the abomasum and the ileum, thereby releasing the biologically active substances at more appropriate locations along the digestive tract.

Other techniques of making and using the novel coating compositions in accordance with the invention are disclosed in U.S. Pat. Nos. 4,877,621 and 4,876,097, both of which are hereby specifically incorporated by reference.

To illustrate the nature of the invention, the following examples are given. It should be understood, however, that the invention is not to be limited to the specific conditions or details set forth in these examples.

EXAMPLES 1 TO 4

Four different compositions with varying formulations of zein (70 grams), pure stearic acid (45 grams), ethylcellulose (15 grams) and talc (steanic 005) as set forth in Table 1 were dissolved in mixtures of dichloromethane (500 cc) and absolute ethanol (500 cc).

The suspensions obtained were sprayed by the "spray-coating" technique onto methionine (350 grams) in the form of granules whose average diameter were between 0.63 and 0.80 mm.

For each composition used, the methionine titre of the coated granules, and also the percentage release of methionine after 6 and 24 hours in an aqueous medium buffered to pH 6 at 40° C., were determined.

The release of the methionine contained in the granules obtained was examined, under specified conditions, by stirring a known quantity of granules in a buffered medium maintained at constant pH at a temperature of 40° C. The results are recorded in Table 1.

TABLE 1

| | Coating composition (parts by weight) | | | | Quantity by weight of coating composition coated granule | Methionine titre % | Percentage of methionine released at pH 6 and at 40° C. | |
|---|---|---|---|---|---|---|---|---|
| Examples | Zein | Ethylcellulose | Stearic acid | Talc | | | 6 H | 24 H |
| 1 | 54 | 35 | 11 | 0 | 20 | 78.7 | 3.2 | 7.3 |
| 2 | 50 | 32 | 10 | 8 | 19 | 79.0 | 2.7 | 6.0 |

TABLE 1-continued

| Examples | Coating composition (parts by weight) | | | | Quantity by weight of coating composition coated granule | Methionine titre % | Percentage of methionine released at pH 6 and at 40° C. | |
| --- | --- | --- | --- | --- | --- | --- | --- | --- |
| | Zein | Ethylcellulose | Stearic acid | Talc | | | 6 H | 24 H |
| 3 | 47 | 30 | 10 | 13 | 20 | 78.6 | 3.8 | 8.3 |
| 4 | 44 | 28 | 9 | 19 | 19 | 79.0 | 3.0 | 7.0 |

EXAMPLE 5

Example 1 was repeated, using a formulation of zein F 4000 (by Benzian) (40 grams), stearic acid (25 grams, ethylcellulose N22 (by Hercules) (25 grams), and calcium carbonate (10 grams).

The release of the methionine contained in the granules was determined, under specified conditions, in a buffered medium maintained at constant pH (6 and 2) at a temperature of 40° C. The results are recorded in Table 2.

TABLE 2

| Examples | Coating composition (parts by weight) | | | | Quantity by weight of coating composition coated granule | Methionine titre % | Percentage of methionine released at 40° C. | | | |
| --- | --- | --- | --- | --- | --- | --- | --- | --- | --- | --- |
| | | | | | | | pH 6 | | pH 2 | |
| | Zein | Ethylcellulose | Stearic acid | Talc | | | 6 H | 24 H | 6 H | 24 H |
| 5 | 40 | 25 | 25 | 10 | 20% | 78.5 | 2.0 | 10.0 | 2.0 | 16 |

What is claimed is:

1. A composition for the coating of feed additives for ruminants, consisting essentially of:
   (a) zein;
   (b) a hydrophobic substance;
   (c) an optional non-water-soluble polymer;
   (d) an inorganic filler; and
   (e) wherein said components (a), (b), (c) and (d) are present in amounts such that said composition is stable in the rumen, is not substantially degraded in the abomasum and is substantially degraded primarily by enzymes in the small intestine.

2. The composition of claim 1 wherein said hydrophobic substance is selected from fatty acids, fatty esters, fatty alcohols and mixtures thereof.

3. The composition of claim 2 wherein said fatty acids are selected from stearic acid and behenic acid.

4. The composition of claim 1 wherein said hydrophobic substance has a melting point above about 60° C.

5. The composition of claim 1 wherein said non-water-soluble polymer is selected from non-water-soluble ethers and esters of cellulose, ethylcellulose, cellulose acetate, cellulose propionate, cellulose acetate butyrate, polyvinyl esters, polyvinyl acetate, and mixtures thereof.

6. The composition of claim 5 wherein said non-water-soluble polymer is selected from ethylcellulose and polyvinyl acetate.

7. The composition of claim 1 wherein said inorganic filler is selected from talc, silica, carbonates, complex polyphosphates based on $Na_2O$, $CaO$, $P_2O_5$ and $Al_2O_3$, and mixtures thereof.

8. The composition of claim 1 further comprising a plasticizer.

9. The composition of claim 8 wherein said plasticizer is selected from triacetin, butylphthalate, sodium oleate, propylene glycol, and mixtures thereof.

10. The composition of claim 1 wherein composition contains by weight in the range of about 10 to about 90% of said zein; in the range of about 10 to about 90% of said hydrophobic substance, in the range of about 0 to 80% of said non-water-soluble polymer, and in the range of about 5 to about 300% of said inorganic filler calculated relative to the combined weight of said zein, said hydrophobic substance and said non-water-soluble polymer.

11. The composition of claim 1 wherein said composition contains by weight in the range of about 30 to about 80% of said zein, in the range of about 10 to about 70% of said hydrophobic substance, in the range of about 0 to 70% of said non-water-soluble polymer and in the range of about 5 to about 150% of said inorganic filler calculated relative to the combined weight of said zein, said hydrophobic substance and said non-water-soluble polymer.

12. A feed additive intended for ruminants, consisting essentially of a core of a biologically active substance surrounded by a substantially continuous film of a coating composition comprising (a) zein, (b) a hydrophobic substance, (c) an optional non-water-soluble polymer and (d) an inorganic filler, wherein said components (a), (b), (c) and (d) are present in amounts such that said composition is stable in the rumen, is not substantially degraded in the abomasum and is substantially degraded primarily by enzymes in the small intestine.

13. The feed additive of claim 12 wherein said feed additive is selected from medicinal products, vitamins and amino acids.

14. The feed additive of claim 13 wherein said feed additive is selected from methionine, lysine, and vitamin A.

15. The feed additive of claim 12 wherein said biologically active substance comprises in the range of, by total weight, about 40 to about 95% of said feed additive.

16. The feed additive of claim 12 wherein said feed additive is in the form of a granule.

17. The feed additive of claim 16 wherein said coating composition comprises in the range of about 5% to about 60% by total weight of said granules.

18. The feed additive of claim 16 wherein said granules have a size in the range of about 0.1 to about 5 mm.

19. The feed additive of claim 18 wherein said granules have a size in the range of about 0.6 to about 2 mm.

20. A method of administering a biologically active substance to a ruminant, comprising the step of orally administering to said ruminant a sufficient amount of granules containing said biologically active substance to deliver an effective amount of said biologically active substance, said granules comprising a core of said biologically active substance surrounded by a substantially continuous film of a coating comprising (a) zein, (b) a hydrophobic substance, (c) an optional non-water-soluble polymer and (d) an inorganic filler, wherein said components (a), (b), (c) and (d) are present in amounts such that said composition is stable in the rumen, is not substantially degraded in the abomasum and is substantially degraded primarily by enzymes in the small intestine.

21. The method of claim 20 wherein said biologically active substance is selected from medicinal products, vitamins and amino acids.

22. The method of claim 20 wherein said oral administration is in the form of feed additives.

* * * * *